United States Patent
Krebs

(10) Patent No.: US 9,719,939 B2
(45) Date of Patent: Aug. 1, 2017

(54) APPARATUS AND METHOD FOR INSPECTING PRINTED IMAGES

(71) Applicant: Stephan Krebs, Landsberg am Lech (DE)

(72) Inventor: Stephan Krebs, Landsberg am Lech (DE)

( * ) Notice: Subject to any disclaimer, the term of this patent is extended or adjusted under 35 U.S.C. 154(b) by 315 days.

(21) Appl. No.: 14/379,236

(22) PCT Filed: Feb. 8, 2013

(86) PCT No.: PCT/EP2013/052560
§ 371 (c)(1),
(2) Date: Nov. 20, 2014

(87) PCT Pub. No.: WO2013/120782
PCT Pub. Date: Aug. 22, 2013

(65) Prior Publication Data
US 2015/0077538 A1    Mar. 19, 2015

(30) Foreign Application Priority Data
Feb. 17, 2012   (DE) .......... 10 2012 101 310

(51) Int. Cl.
*H04N 9/47* (2006.01)
*H04N 7/18* (2006.01)
(Continued)

(52) U.S. Cl.
CPC ......... *G01N 21/8803* (2013.01); *G01N 21/86* (2013.01); *G01N 21/8901* (2013.01);
(Continued)

(58) Field of Classification Search
CPC ................ G01N 21/8806; G01N 21/86; G06T 2207/30144
(Continued)

(56) References Cited

U.S. PATENT DOCUMENTS 5,256,883 A   10/1993   Weichmann et al.
6,050,192 A   4/2000   Kipphan et al.
(Continued)

FOREIGN PATENT DOCUMENTS

CN   101879507 A   11/2010
DE   4136461 A1   5/1993
(Continued)

OTHER PUBLICATIONS

"Kombinierte Matrix-Zeilenkamera UK 1155-Z (Matrix/Line Camera UK1155-Z)," ABS GmbH Jena, Automatisierung Bildverarbeitung Software, http://www.kameras.abs-jena.de/produkte/kamera_uk1155-z_zeilenkamera_de.html, retrieved on Jun. 28, 2013.

(Continued)

*Primary Examiner* — Hung Dang
*Assistant Examiner* — Girumsew Wendmagegn
(74) *Attorney, Agent, or Firm* — Slater Matsil, LLP

(57) ABSTRACT

An apparatus can be used for inspecting printed images for a printing or finishing machine with continuously moved printed products. An illumination unit with a light source illuminates a recording region and an image capture apparatus with at least one camera, for example a line scanning camera, is set up to capture an image inside the recording region, which extends over the width of the printed product, wherein the image capture apparatus is set up to generate a multi-line partial image.

20 Claims, 8 Drawing Sheets

(51) Int. Cl.
  *G01N 21/88* (2006.01)
  *G06T 7/00* (2017.01)
  *G01N 21/86* (2006.01)
  *G01N 21/89* (2006.01)

(52) U.S. Cl.
  CPC .. *G06T 7/0008* (2013.01); *G06T 2207/10004* (2013.01); *G06T 2207/10152* (2013.01); *G06T 2207/30144* (2013.01)

(58) Field of Classification Search
  USPC .......................................................... 348/88
  See application file for complete search history.

(56) References Cited

U.S. PATENT DOCUMENTS

| | | | |
|---|---|---|---|
| 7,635,830 | B2 | 12/2009 | Diederichs |
| 7,784,975 | B2 | 8/2010 | Krebs et al. |
| 8,237,828 | B2 | 8/2012 | Tatarczyk et al. |
| 8,272,324 | B2 | 9/2012 | Müller et al. |
| 8,476,611 | B2 | 7/2013 | Eisen |
| 8,817,091 | B2 | 8/2014 | Koltermann et al. |
| 2001/0042847 | A1 | 11/2001 | Eisen et al. |
| 2006/0239510 | A1 | 10/2006 | Tatarczyk et al. |
| 2008/0164430 | A1* | 7/2008 | Diederichs ......... G01N 21/8901 250/559.08 |

FOREIGN PATENT DOCUMENTS

| | | |
|---|---|---|
| DE | 4321179 A1 | 1/1995 |
| DE | 19847666 A1 | 4/2000 |
| DE | 102004014532 B3 | 3/2005 |
| DE | 102004033660 A1 | 2/2006 |
| DE | 102005005303 A1 | 7/2006 |
| DE | 102005018855 A1 | 11/2006 |
| DE | 102008015039 A1 | 9/2009 |
| DE | 102008064390 A1 | 7/2010 |
| DE | 102010020824 A1 | 1/2011 |
| DE | 202010008084 U1 | 12/2011 |
| DE | 102011111355 A1 | 2/2013 |
| EP | 1154225 A1 | 11/2001 |
| EP | 2003443 A1 | 12/2008 |
| EP | 2011755 A1 | 1/2009 |
| EP | 2093173 A1 | 8/2009 |
| EP | 2208987 A1 | 7/2010 |
| JP | 2005188929 A | 7/2005 |
| JP | 2006105844 A | 4/2006 |
| WO | 2011055432 A1 | 5/2011 |

OTHER PUBLICATIONS

"Digital Monochrome (b/w) Progressive Scan Camera With Enhanced NIR Sensitivity—Baumer HXG20NIR/HXG20NIR-F" Baumer Optronic GmbH, Technical Data HXG20NIR, Feb. 1, 2012 pp. 1-15.

"MetaLight DT Series: DT401—Dome Light," Metaphase Technologies Inc., http://www.metaphase-tech.com, retreived on Jul. 10, 2013, 1 page.

"Diffuse Dome/Tube Lights," Metaphase Technologie Inc., Eureca Messtechnik GmbH, http://www.eureca.de/english/optoelectronics_lightings.html#_4, retrevied on Jul. 10, 2013, 2 pages.

"MetaBright Diffuse Tube Lights—LED Tubular Diffuse Illuminators," Metaphase Technologies, Inc., http://www.metaphase-tech.com/userfiles/file/upload_repository/Diffuse_Tube_Lights_Brochure.pdf, retrieved on Jul. 10, 2013, 4 pages.

Metcalfe, L., "Choosing High-Speed Surface Inspection Sensors," Advanced Imaging, Feb. 2008, 3 pages.

"Partial Scan Image Capture Increases Speed of Vision Processing," Automation Trends, Omron Electronics, Nov. 2003, 2 pages.

"Tunnel Lights" LATAB—Industrial LED Lighting, http://www.latab.net/int/products/lighting-heads/tunnel-lights/, retrieved on Jul. 10, 2013, pp. 11.

"Professionelle Lichtsysteme für die industrielle Bildverarbeitung—Tunnel M (Professional lighting systems for industrial imaging—Tunnel-M)," Büchner Lichtsysteme GmbH, Version 2, http://www.buechner-lichtsysteme.de/index.php/de/produkte/tunnelbeleuchtungen, retrieved on Sep. 23, 2014.

"Licht nicht nur am Ende des Tunnels (Light, not only at the end of the tunnel)," Stemmer Imaging, news@imaging, Oct. 2011, pp. 9.

* cited by examiner

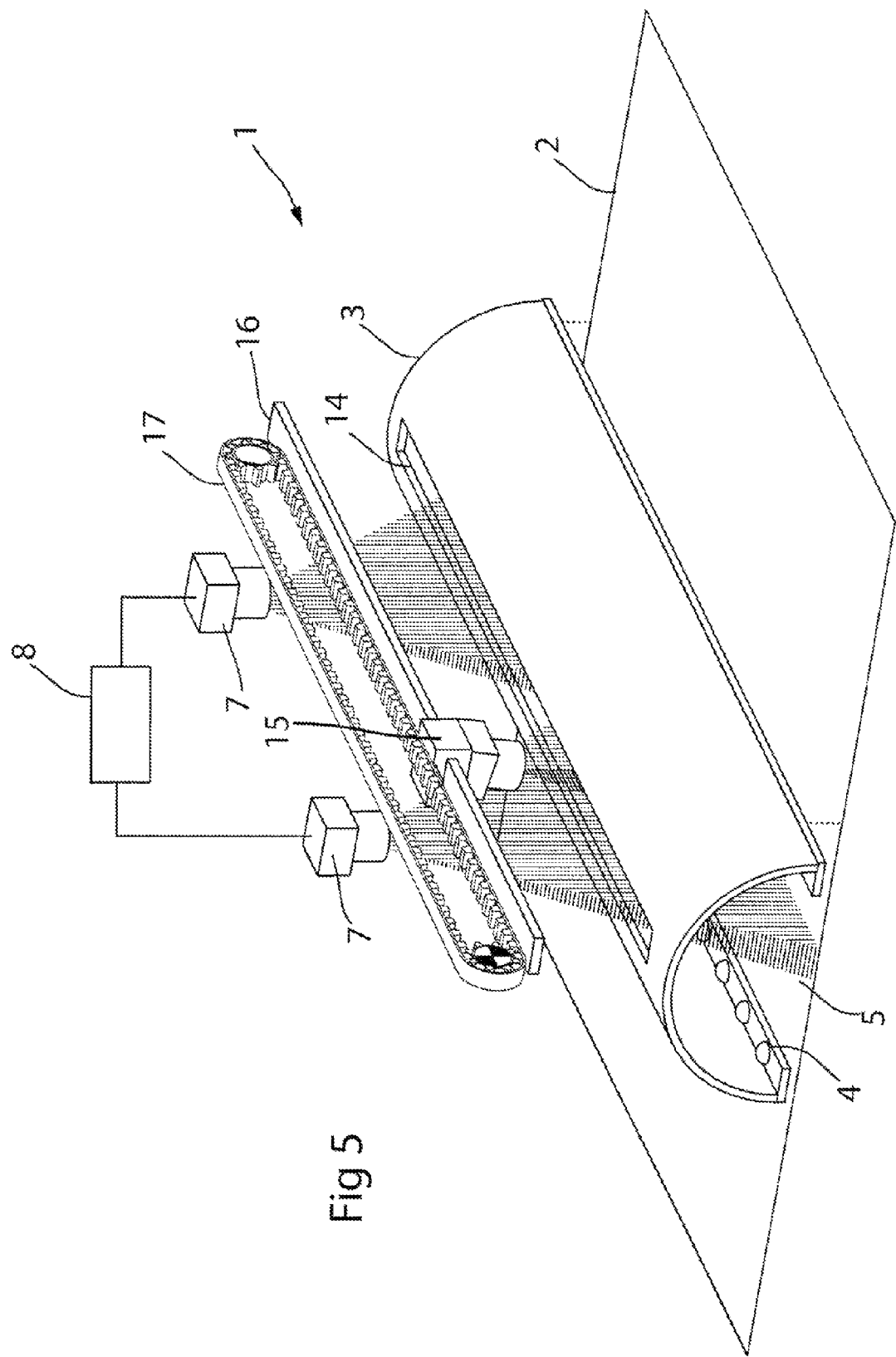

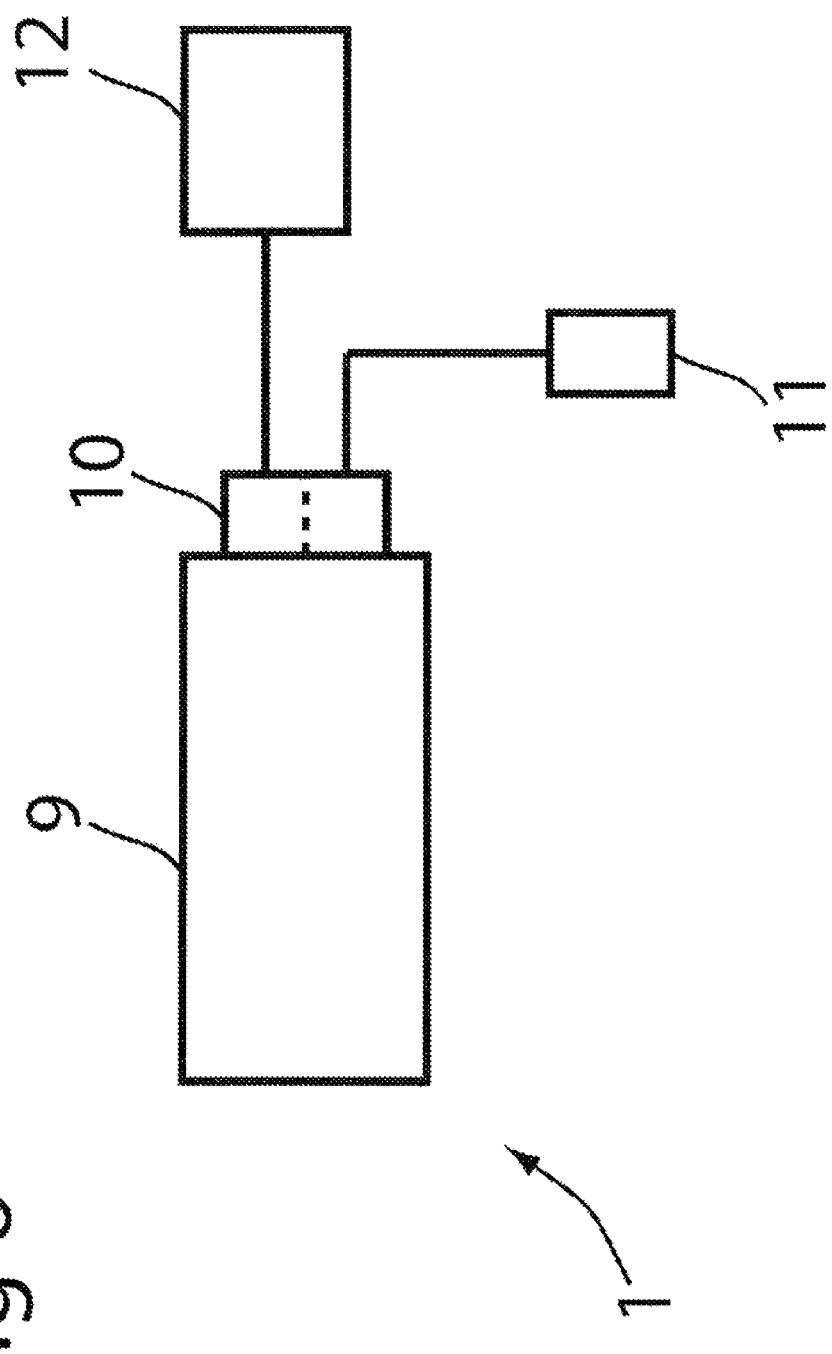

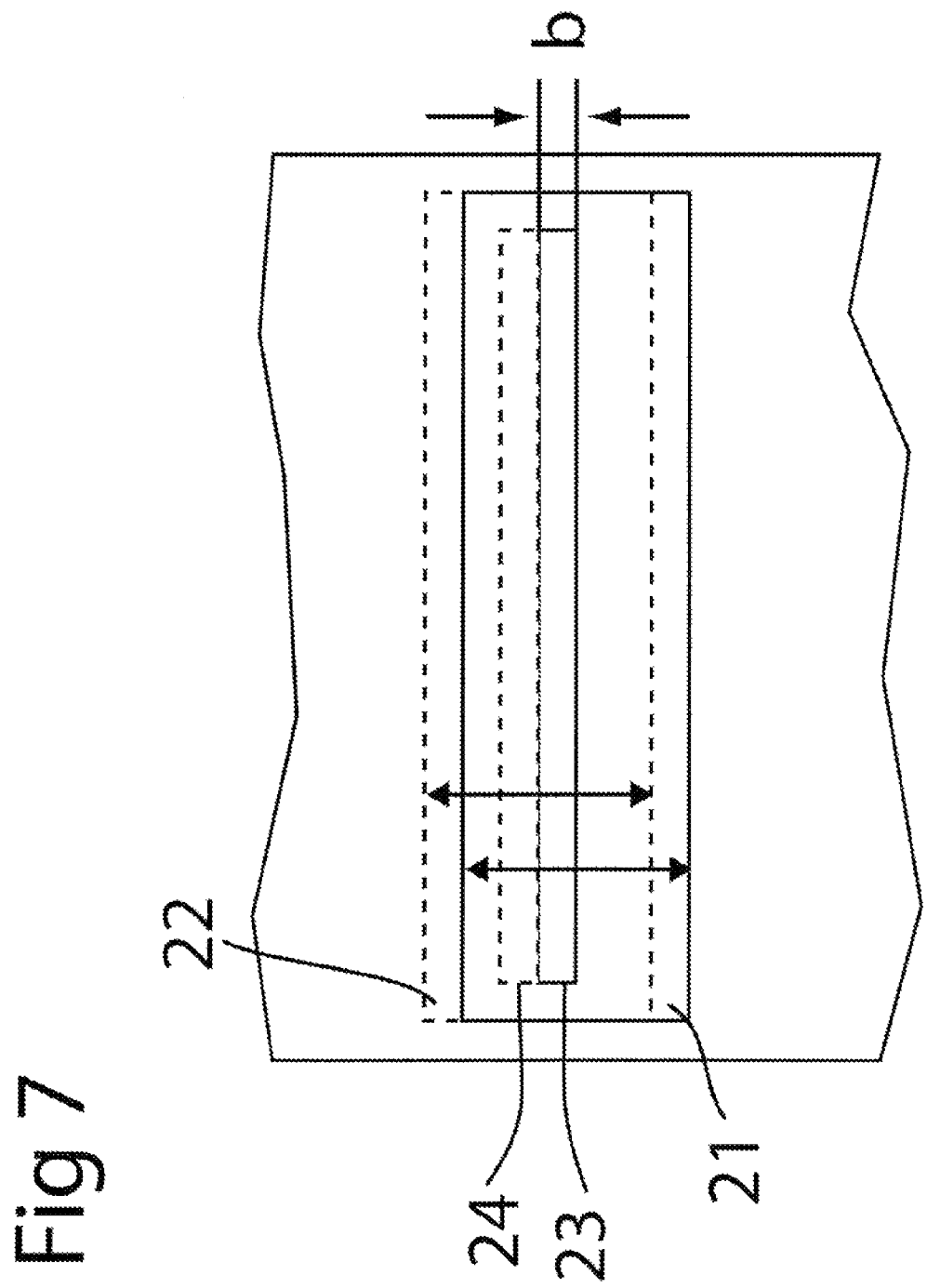

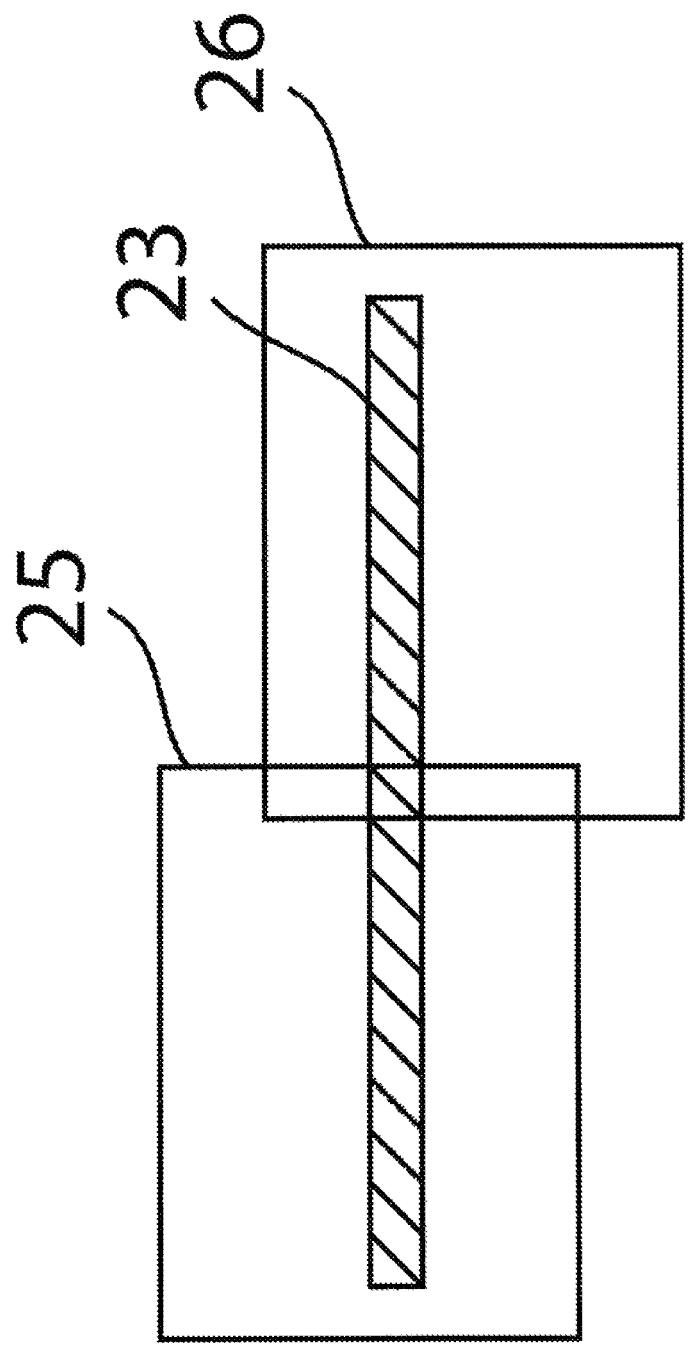

APPARATUS AND METHOD FOR INSPECTING PRINTED IMAGES

This patent application is a national phase filing under section 371 of PCT/EP2013/052560, filed Feb. 8, 2013, which claims the priority of German patent application 10 2012 101 310.1, filed Feb. 17, 2012, each of which is incorporated herein by reference in its entirety.

TECHNICAL FIELD

The invention relates to an apparatus and method for inspecting printed images.

BACKGROUND

Apparatuses and methods are used when visualizing and inspecting printed webs or printed sheets. After printing, it is necessary to check the printed result for the purposes of quality assurance. According to a first possibility, the sheets or webs are moved through under video cameras, in which case the video cameras record an image and an operator can check this. In addition, use is also made of automatic image checking systems in which a computer carries out an image comparison.

In particular applications, for example, in so-called finishing machines for the label industry, the demands imposed on print inspection are generally not particularly high and so discrete optical sensors for detecting missing labels or gross errors are often used here. This non-imaging automatic rough inspection is normally assisted by a manual inspection with the aid of a stroboscope. The quality of this inspection method substantially depends on the capabilities of the machine operator. In addition, the use of stroboscopes harbors health risks such as epilepsy, eye damage, etc.

In video systems, use is nowadays made of traversing video cameras which approach the desired position within the print repeat using positioning drives or else manually and record images there in a flash-controlled manner. These images are then transferred to a superordinate computer where they are processed further—for example, the print can be evaluated or inspected in terms of color, position and content—and are then displayed on a screen.

During operation, the operator is able to display the approached position in an enlarged manner. He can either obtain an extensive impression of the print quality, in particular with respect to the color, using a zoom factor of 1.0 or can check the quality of the printing raster and the register accuracy using high magnification, for example, with a zoom factor of 10 to 16. The zoom function can be achieved in two ways: either the use of a motorized zoom lens or the combination of two imaging sensors in order to achieve electronic zoom using CCD or CMOS cameras. The latter principle is disclosed in U.S. Patent Publication No. 2006/0239510 A1 and EP Patent No. 2003443 A1.

Traversing video cameras with mechanical or electronic zoom record only a relatively small area of the printed material flow. This is in practice only a few percent, which is why the systems are rather poorly suited to inspecting the print. Use is additionally made of matrix cameras which, however, presuppose extensive homogeneous illumination. This cannot be achieved in practice, in particular for highly reflective materials or holograms. Therefore, errors in the printed image cannot be reliably detected, whether it is not possible to clearly determine whether an abnormality can be attributed to an error or reflection.

There are also special line scan cameras, but these are expensive. The advantage of line scan cameras is that highly reflective materials or holograms can also be recorded when recording a single line.

SUMMARY

The invention relates to an apparatus for inspecting printed images for a printing or finishing machine with continuously moved printed products, having an illumination unit with a light source for illuminating a recording region, and an image capture apparatus with at least one camera which is set up to capture an image inside the recording region, which image extends over the width of the printed product.

The invention also relates to a method for inspecting printed images in a printing or finishing machine.

Embodiments of the invention provide an apparatus and a method which can be used to reliably inspect printed images even in the case of reflective materials or holograms. The apparatus can also have a mechanically simple, cost-effective and compact design.

With respect to the apparatus, an apparatus of the type mentioned at the outset which is characterized in that the image capture apparatus is set up to generate a multi-line partial image.

Therefore, in the apparatus according to the invention, the entire region or at least a large part of the region recorded by the camera is not evaluated, but rather deliberately only a multi-line partial image which is also referred to as a strip below. In the case of a strip, it is possible for very good diffuse, homogeneous illumination to exist in this strip-shaped region, with the result that interfering reflections do not occur.

In comparison with a line scan camera, there is the advantage that matrix cameras, as cameras for recording a 2D image, are considerably more cost-effective and such multi-line strips can also improve the further processing.

In the apparatus according to the invention, it is particularly advantageous that it can be used for different tasks:
 replacing a stroboscope on a finishing machine,
 replacing the missing label detection on the finishing machine, and
 replacing the traversing video system on the printing or finishing machine.

In one development of the invention, the light source is operated in a pulsed manner. For this purpose, the image capture apparatus is preferably set up to control the light source in such a manner that the image capture and the illumination of the recording region by the light source are carried out in a manner temporally matched to one another. In such a refinement, the switched-on duration of the light source can be greatly reduced, with the result that the generation of heat, in particular, is reduced to such an extent that it is possible to dispense with complicated cooling measures.

An embodiment method can be used for inspecting printed images in a printing or finishing machine with continuously moved printed products by means of at least one 2D camera. A first image is captured. The width of the image extends over substantially the entire width of the printed product. A second image is repeatedly captured. The width of the second image extends over substantially the entire width of the printed product, after the printed product has respectively moved on by a predetermined transport distance (b). The printed product is illuminated while an image is being captured and is switched off in periods in between.

A particular advantage of the method according to the invention is that more and more lines can be recorded and processed at the same time and ideally diffuse illumination can be ensured in the process.

BRIEF DESCRIPTION OF THE DRAWINGS

The invention is explained in more detail below using figures, in which:

FIG. 5 shows the apparatus from FIG. 4 with an additional adjustable camera;

FIG. 6 shows a schematic illustration of the coupling of an image capture apparatus according to the invention to a printing or finishing machine and/or a sensor;

FIG. 7 shows a schematic illustration for visualizing the recording of strip-shaped partial images; and FIG. 8 shows a schematic illustration for visualizing the generation of a strip-shaped partial image from the images from two cameras.

DETAILED DESCRIPTION OF ILLUSTRATIVE EMBODIMENTS

Figure 1:
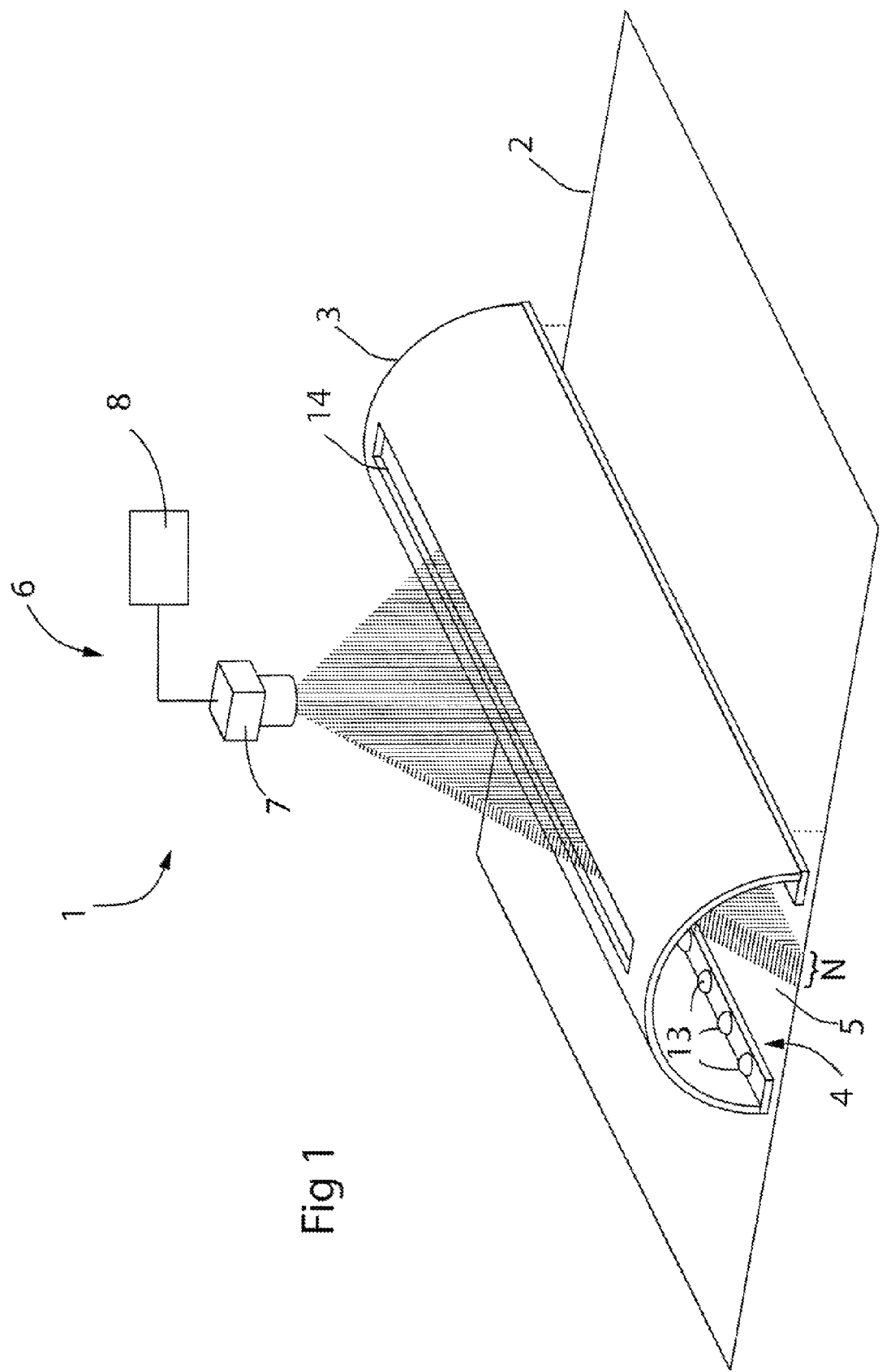
FIG. 1 shows an apparatus according to the invention for inspecting printed images with a camera.

FIG. 1 shows an apparatus according to the invention for inspecting printed images, having an illumination unit 3 in which a multiplicity of light-emitting diodes 13 are used as the light source 4. These light-emitting diodes are arranged inside a tunnel 12, with the result that the tunnel 12 is illuminated from the inside by the light-emitting diodes 13. A strip of LEDs 13 is preferably situated on each of the lower edges of the tunnel 12. The material of the tunnel 12 consists of a diffusely reflective material or is coated with a diffusely reflective material on the inside, with the result that homogeneous illumination is produced inside the tunnel. The tunnel 12 substantially has the shape of a half-cylinder, the open section surface pointing downward in order to illuminate a so-called print repeat there. This print repeat has the printed products and consists of a long web or a sheet, depending on what type of printing or finishing machine is used and what is intended to be printed. This print repeat is moved through under the tunnel, preferably in a continuous movement. A slot 14 is situated on the top side of the tunnel 12 in order to make it possible to record an image of the print repeat 2 from outside the tunnel.

As described at the outset, the quality of the printed image must be checked in printing or finishing machines, which can be carried out with the apparatus according to the invention in a semi-automatic or fully automatic manner. In order to record the image itself, the image capture apparatus has a camera 7 with a CMOS camera chip. The latter makes it possible to define a variable image format. According to the invention, the camera 7 records a strip with a number of lines N, the number of lines N being selected to be relatively small. As can be discerned from FIG. 1, the image strip intended for further processing is relatively narrow and is in the center of the tunnel. Virtually ideal diffuse illumination can be achieved in such a narrow region, with the result that reflections do not occur.

The region which is or can be optically captured by the camera is larger than the strip with the number of lines N, but the image recorded by the camera 7 can be processed further in such a manner that only the strip with the number of lines N is used. In this exemplary embodiment, the number of lines N is 100, in which case a line width is typically 0.1 to 0.2 mm. The height of the recorded image strip is therefore 10 to 20 mm. In the case of printed products which are less problematic with respect to reflections, a larger width could be selected, for example, 30 mm corresponding to a number of lines of 150 to 300, depending on the width of a line. In the case of very difficult materials such as holograms, the number of lines could also be selected to be smaller, for example, 50, which produces a strip width of 5 to 10 mm.

The camera 7 is connected to an image processing unit 8 which combines the strip-shaped images recorded by the camera 7 and provides an overall image of a larger region.

Figure 2:
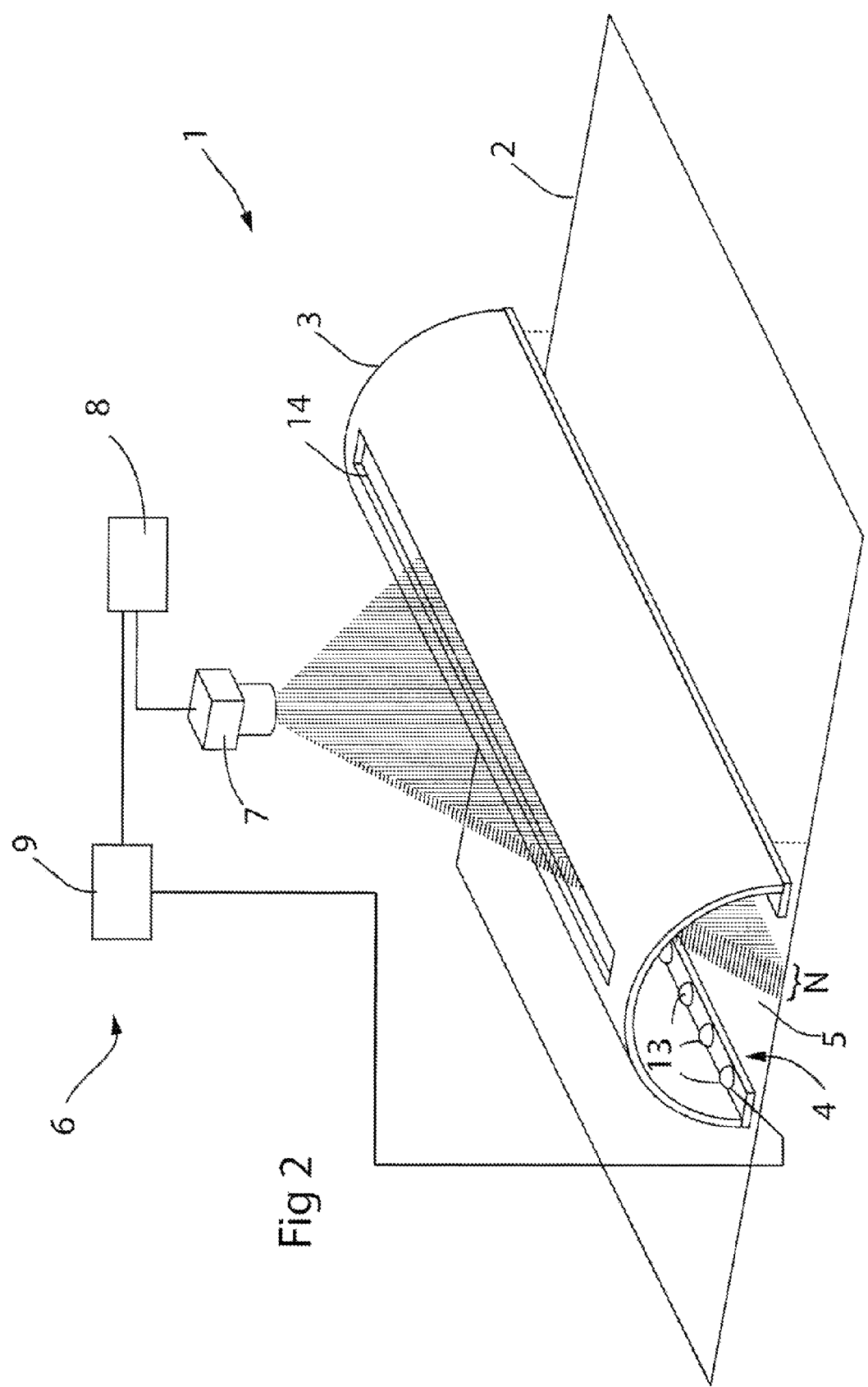
FIG. 2 shows the apparatus from FIG. 1 with an enhanced image processing unit.

FIG. 2 shows the apparatus for inspecting printed images from FIG. 1, in which case the illumination unit 3 or its light source 4 is controlled via a control unit 9 in such a manner that the light source 4 can be operated in a pulsed manner. In this case, the recording of the strip-shaped images by the camera 7 is matched to the control of the light source 4 in such a manner that the illumination is always switched on when recording an image and is switched off in the periods in between.

Figure 3:
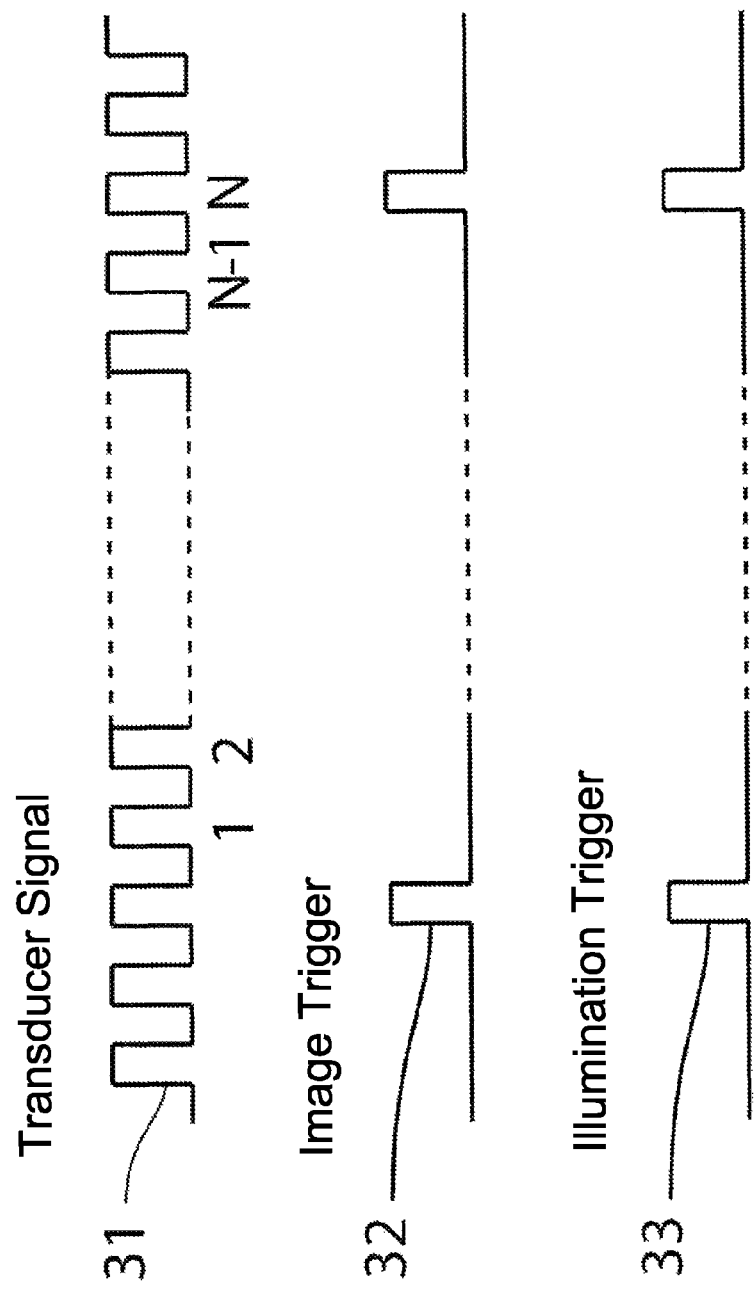
FIG. 3 shows a signal diagram for controlling the camera and light source.

The control signals are illustrated in FIG. 3. A transducer signal 31 indicates the speed at which the print repeat is moved along, in which case one pulse represents the onward movement of the print repeat by one line. The strip width is intended to be N, with the result that, in order to completely capture the print repeat, it is necessary to record an image as soon as the print repeat has moved on by N lines. The second signal in the signal diagram is an image trigger 32, that is to say image recording is triggered every N lines. The third line in the signal diagram indicates an illumination trigger 33 which switches on the light source 4 in synchronism with the image trigger 32 if an image is intended to be recorded. In modifications of these embodiments, the illumination duration can be set in such a manner that it is already switched on at N−1, for example, and is only switched off again at N+1, with the result that timing problems between illumination and image recording are avoided.

The recording of image strips and pulsed illumination matched thereto produce a much higher efficiency than a line scan camera because the illumination must be pulsed only every N lines. The illumination is usually switched on constantly in line scan cameras. The power consumed for illumination corresponds only to 1:N of the power consumed in a line scan camera. This is important not only in terms of general energy-saving aspects but is important, in particular, because it is possible to dispense with complicated cooling of the light source 4, that is to say the LEDs 13 in this exemplary embodiment, as a result. As a result, the illumination unit becomes more cost-effective and also more compact, in particular.

An overall image can be subsequently assembled from the strip-shaped images, which overall image can be displayed on a screen and can be used for print inspection.

If a camera with a high image rate is used, a stroboscope can be replaced with this arrangement. At the same time, new possibilities open up as a result of the homogeneous display over the entire width of the material flow. Conventional stroboscope flash tubes are relatively short and cannot be used in broader applications. The function of missing label detection when used to detect errors in printed labels and further print inspection functions can be achieved by evaluating the image data for each repeat.

Figure 4:
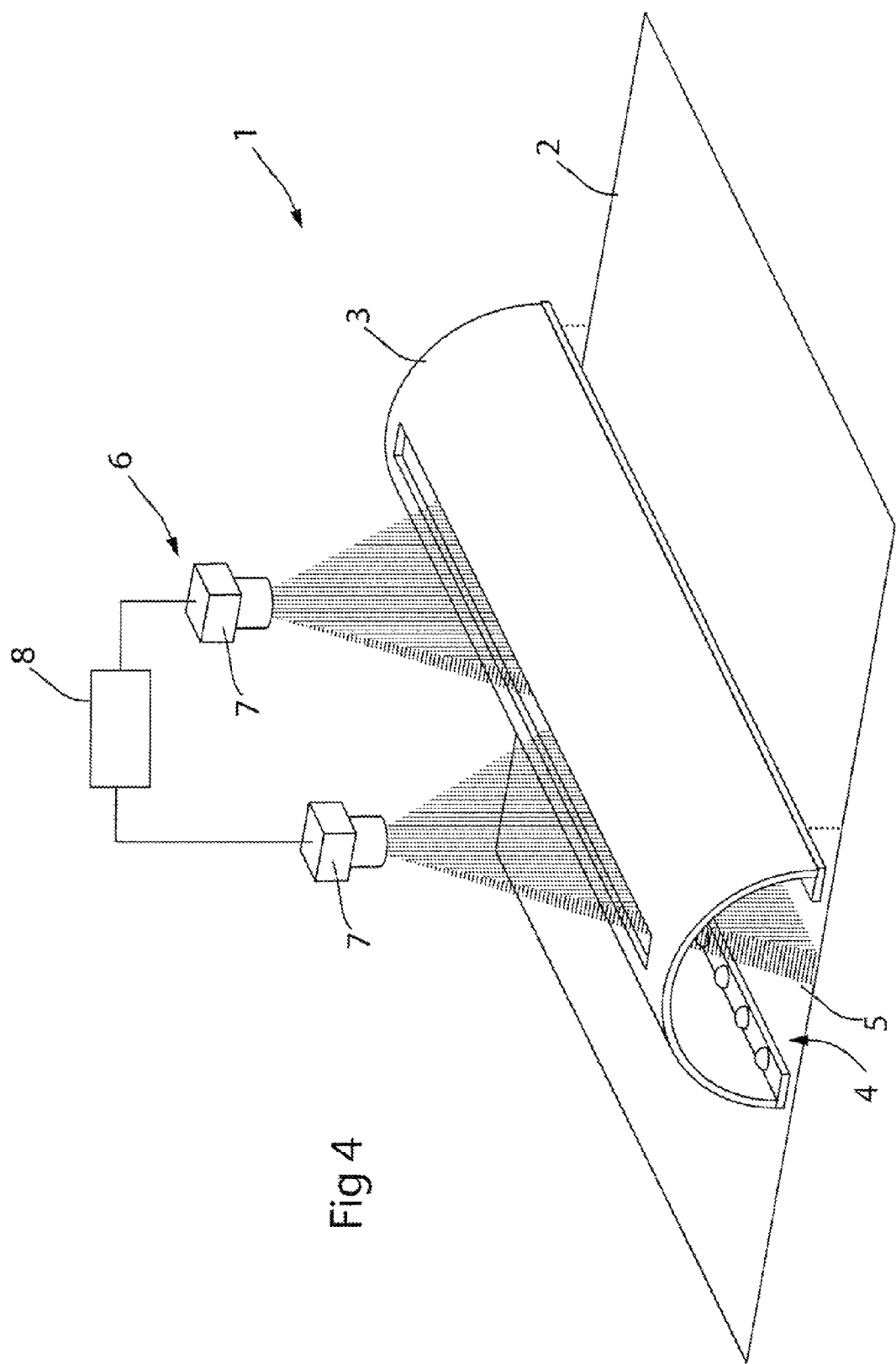
FIG. 4 shows an apparatus according to the invention for inspecting printed images with two cameras.

FIG. 4 shows an enhanced arrangement in which two cameras 7 are used. This is useful if the width of the print repeat is relatively large, with the result that the operating range of an individual camera 7 does not suffice. The cameras 7 are either aligned with respect to one another in such a manner that the recorded images adjoin one another or the image processing unit 8 controls the evaluation of the image signals from the two cameras 7 in such a manner that only the image signal from one camera is used in the overlapping region. An offset of the recorded image regions can also be compensated for in this manner. The two cameras 7 result in a strip of an increased length, in which case this principle can be enhanced as desired by means of further cameras.

The use of a plurality of cameras can be used to avoid distortions produced by the camera optics in the edge region of the respectively recorded images. In this case, use is made of only part of the theoretically possible operating range in which the distortions are relatively small. Since CMOS cameras are relatively cost-effective, they can be used to achieve a virtually distortion-free image over the entire width without the need for a complicated electronic correction.

In some applications, it is necessary to be able to zoom into the printed image in order to be able to also check details in the printed image. A further camera 15 is provided for this purpose in one development of the exemplary embodiment from FIG. 4, which is shown in FIG. 5, which further camera is displaceably mounted on a crossmember 16 and can be displaced using a toothed belt 17. This camera 15 can also be used to generate greatly magnified image excerpts. The advantages of the homogeneously diffuse light can be equally used by all CMOS cameras 7 and 15. The entire arrangement is nevertheless very compact and can be implemented with a low overall height.

FIG. 6 shows the coupling of a control device 9 of the apparatus 1 according to the invention for inspecting printed images to a printing or finishing machine 12 or a sensor 11. For this purpose, the control device 9 is equipped with an interface 10. It is therefore possible to obtain a signal, for example, in the form of the transducer signal from FIG. 3, from a printing or finishing machine, which signal indicates the movement speed of the print repeat 2. As a result, the control device 9 can determine the frequency at which images must be recorded. Alternatively, a sensor 11 which measures the movement speed can be provided.

FIG. 7 shows a schematic illustration of how strip-shaped images can be recorded as an excerpt of an image region which can be captured by a camera 7. FIG. 7 relates to the arrangement from FIG. 1 in which one camera 7 is used. An image 21 is first of all recorded. A strip 23 inside this image 21 is selected, in which case edge regions of the image 21 are cut off. This strip-shaped partial image 23 can be generated by further processing only particular pixels of the image sensor of the camera 7. After the print repeat has moved on by the width b of a strip, a second image 22 is recorded from which a strip-shaped partial image 24 (illustrated using dashed lines in FIG. 7) is in turn processed further. This method is continued, with the result that an overall image is produced from the stringing-together of the partial images 23 and 24.

FIG. 8 illustrates how a strip-shaped partial image 23 can be generated from the recorded images from two cameras 7, as is carried out in the exemplary embodiment from FIG. 4. The images 25 and 26 which are recorded by the two cameras 7 overlap. The overlapping region can be measured or can be calculated from the two images 25 and 26 by means of an electronic method. A contiguous strip-shaped partial image 23 can be determined by evaluating the corresponding pixels of the two cameras 7.

In all variants, the result is a sequence of strip-shaped partial images or the image capture apparatus 6 is already set up to assemble an overall image from the strip-shaped partial images. This overall image can be displayed on a screen and can be checked by an operator. Fully automatic printed image inspection can also be achieved by virtue of a computer comparing the recorded image with a reference image. Depending on the algorithm used, it would also be possible to already compare the strip-shaped partial images with reference images.

Further modifications and refinements of the invention are at the discretion of a person skilled in the art and are included in the claims.

The invention claimed is:

1. An apparatus for inspecting printed images for a printing or finishing machine with a continuously moving printed product, the apparatus comprising:
   an illumination unit with a light source for illuminating a recording region, wherein the illumination unit has a tunnel that is illuminated on an inside by the light source, wherein the tunnel has a tunnel wall on the inside comprising a diffusely reflective material and a slot on its top side in a longitudinal direction of the tunnel, and wherein the light source has a plurality of LEDs arranged inside the tunnel; and
   an image capture apparatus with a camera unit that is set up to capture an image inside the recording region, wherein the image extends over a width of the printed product, and wherein the image capture apparatus is set up to generate a multi-line partial image.

2. The apparatus as claimed in claim 1, wherein the partial image is an excerpt from an image region, the camera unit configured to capture the image region.

3. The apparatus as claimed in claim 1, wherein the image capture apparatus is set up to connect a plurality of generated partial images to form an overall image.

4. The apparatus as claimed in claim 1, wherein the light source is operated in a pulsed manner.

5. The apparatus as claimed in claim 4, wherein the image capture apparatus is set up to control the light source in such a manner that an image capture and an illumination of the recording region by the light source are carried out in a manner temporally matched to one another.

6. The apparatus as claimed in claim 1, wherein the image capture apparatus has an interface for connection to a sensor or a control apparatus of the printing or finishing machine and is set up to control the image capture apparatus in a manner matched to a movement speed of the printed product.

7. The apparatus as claimed in claim 1, wherein the camera unit comprises a plurality of cameras arranged along the slot and set up to record two images that are beside one another or partially overlap.

8. The apparatus as claimed in claim 7, wherein the cameras are CMOS cameras.

9. The apparatus as claimed in claim 7, further comprising an additional camera that is movable above the slot.

10. The apparatus as claimed in claim 1, wherein the camera unit comprises at least one CMOS camera.

11. An apparatus for inspecting printed images for a printing or finishing machine with a continuously moving printed product, the apparatus comprising:
   an illumination unit with a light source for illuminating a recording region inside the illumination unit, wherein the illumination unit has a slot;
   an image capture apparatus with a camera unit that is set up to capture an image inside the recording region, wherein the image extends over a width of the printed product and wherein the image capture apparatus is set up to generate a multi-line partial image; and
   an additional camera located outside the illumination unit and movable above the slot.

12. The apparatus as claimed in claim 11, wherein the partial image is an excerpt from an image region that is captured by the camera unit.

13. The apparatus as claimed in claim 11, wherein the image capture apparatus is set up to connect a plurality of generated partial images to form an overall image.

14. The apparatus as claimed in claim 11, wherein the light source is operated in a pulsed manner.

15. The apparatus as claimed in claim 14, wherein the image capture apparatus is set up to control the light source in such a manner that an image capture and an illumination of the recording region by the light source are carried out in a manner temporally matched to one another.

16. The apparatus as claimed in claim 11, wherein the image capture apparatus has an interface for connection to a sensor or a control apparatus of the printing or finishing machine and is set up to control the image capture apparatus in a manner matched to a movement speed of the printed product.

17. The apparatus as claimed in claim 11, wherein the illumination unit has a tunnel that is illuminated on the inside by the light source, wherein the tunnel has a tunnel wall on the inside comprising a diffusely reflective material and the slot on its top side in a longitudinal direction of the tunnel, and wherein the light source has a plurality of LEDs arranged inside the tunnel.

18. The apparatus as claimed in claim 11, wherein the camera unit comprises a plurality of cameras arranged along the slot and set up to record two images that are beside one another or partially overlap.

19. The apparatus as claimed in claim 18, wherein the cameras are CMOS cameras.

20. The apparatus as claimed in claim 11, wherein the camera unit comprises at least one CMOS camera.

* * * * *